(12) United States Patent
Kang et al.

(10) Patent No.: US 9,900,458 B2
(45) Date of Patent: Feb. 20, 2018

(54) METHOD AND APPARATUS TO CAPTURE MICROFLUIDIC TEST IMAGE

(71) Applicant: SAMSUNG ELECTRONICS CO., LTD., Suwon-si (KR)

(72) Inventors: Kyu Tae Kang, Suwon-si (KR); Se Do Gwon, Goyang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 301 days.

(21) Appl. No.: 14/627,643

(22) Filed: Feb. 20, 2015

(65) Prior Publication Data

US 2015/0244932 A1    Aug. 27, 2015

(30) Foreign Application Priority Data

Feb. 21, 2014  (KR) ........................ 10-2014-0020660

(51) Int. Cl.
  *H04N 1/024*  (2006.01)
  *B01L 3/00*  (2006.01)
  *F16K 99/00*  (2006.01)
  *G01N 35/00*  (2006.01)
  *G01N 35/10*  (2006.01)

(52) U.S. Cl.
  CPC ........ *H04N 1/024* (2013.01); *B01L 3/502738* (2013.01); *F16K 99/00* (2013.01); *F16K 99/0032* (2013.01); *F16K 99/0044* (2013.01); *G01N 35/00069* (2013.01); *G01N 35/1016* (2013.01); *B01L 2200/025* (2013.01); *B01L 2200/14* (2013.01); *B01L 2300/0803* (2013.01); *B01L 2400/0409* (2013.01); *B01L 2400/0677* (2013.01); *G01N 2035/00247* (2013.01); *G01N 2035/1034* (2013.01)

(58) Field of Classification Search
  CPC .............. G01N 35/00069; H04N 1/024; B01L 2200/025; B01L 2300/0803; B01L 2200/14

See application file for complete search history.

(56) References Cited

U.S. PATENT DOCUMENTS 5,892,577 A * 4/1999 Gordon ................ G01N 21/253
356/73
2003/0054563 A1* 3/2003 Ljungstrom ....... G01N 21/6402
436/172

(Continued)

*Primary Examiner* — Jay Patel
*Assistant Examiner* — Marnie Matt
(74) *Attorney, Agent, or Firm* — Sughrue Mion, PLLC (57) ABSTRACT

Disclosed herein are a test apparatus that photographs a home mark of a microfluidic apparatus by using a camera and determining a position of a home of the microfluidic apparatus by using the camera, and a control method thereof. The method of controlling a test apparatus includes photographing a microfluidic apparatus at a predetermined frame rate by using a camera of the test apparatus while the microfluidic apparatus is rotating at a predetermined speed, acquiring a capture image which includes a home mark of the microfluidic apparatus among a plurality of images acquired by the camera, and acquiring information which relates to an encoder of the test apparatus and which corresponds to the home mark of the capture image and determining a position of a home of the microfluidic apparatus based on the acquired information.

10 Claims, 10 Drawing Sheets

(56) References Cited

U.S. PATENT DOCUMENTS

| | | | |
|---|---|---|---|
| 2008/0138247 A1* | 6/2008 | Inganas | G01N 35/00069 |
| | | | 422/82.05 |
| 2010/0177325 A1* | 7/2010 | Kang | G01N 35/00029 |
| | | | 356/614 |
| 2016/0029619 A1* | 2/2016 | Sun | A01N 1/0252 |
| | | | 435/374 |

* cited by examiner

METHOD AND APPARATUS TO CAPTURE MICROFLUIDIC TEST IMAGE

CROSS-REFERENCE TO RELATED APPLICATION(S)

This application claims priority from Korean Patent Application No. 10-2014-0020660, filed on Feb. 21, 2014 in the Korean Intellectual Property Office, the disclosure of which is incorporated herein by reference in its entirety.

BACKGROUND

1. Field

Exemplary embodiments relate to test apparatuses that perform laboratory tests of biological materials by using microfluidic apparatuses and control methods thereof.

2. Description of the Related Art

A microfluidic apparatus is an apparatus used to perform a biological or chemical reaction by manipulating a small amount of a fluid.

In general, a microfluidic structure performing one independent function in a microfluidic apparatus includes a chamber configured to contain a fluid, a channel through which the fluid flows, and a device configured to control the flow, and the microfluidic structure may be implemented by various combinations thereof. A lap-on-a-chip (LOC) is a device manufactured by arranging microfluidic structures on a chip-shaped substrate to perform a test including immunological and serologic reactions or biochemical reactions on the small chip and to perform multi-stage treatments and manipulations.

In order to cause a fluid to flow and to transfer a fluid in a microfluidic structure, a driving pressure is required. As such a driving pressure, capillary pressure or pressure generated using a separate pump may be used. In recent years, disk-shaped microfluidic apparatuses in which microfluidic structures are arranged on a disk-shaped platform and a series of operations are conducted while causing a flow of a fluid by using a centrifugal force have been suggested. They are referred to as Lab CD or Lab-on a disk. A microfluidic apparatus includes chambers to detect a substance to be analyzed or tested and/or detection materials such as indicator paper.

SUMMARY

Therefore, it is an aspect of one or more exemplary embodiments to provide a test apparatus that acquires an image of a home mark of a microfluidic apparatus by using a camera and determines a position of a home of the microfluidic apparatus by using the image, and a control method thereof.

It is another aspect of one or more exemplary embodiments to provide a test apparatus that controls opening and closing of a valve by using a camera and a control method thereof.

Additional aspects of the exemplary embodiments will be set forth in part in the description which follows and, in part, will be obvious from the description, or may be learned by practice of the exemplary embodiments.

In accordance with one aspect of one or more exemplary embodiments, a method for controlling a test apparatus includes photographing a microfluidic apparatus at a predetermined frame rate by using a camera of the test apparatus while the microfluidic apparatus rotates at a predetermined speed, acquiring a capture image which includes a home mark of the microfluidic apparatus, wherein the acquired capture image is included among a plurality of images acquired by the camera, and acquiring information which relates to an encoder of the test apparatus and which corresponds to the home mark of the capture image, and determining a position of a home of the microfluidic apparatus based on the acquired information.

The photographing of the microfluidic apparatus at the predetermined frame rate may include photographing the microfluidic apparatus at the predetermined frame rate such that successive images partially overlap each other.

The photographing of the microfluidic apparatus at the predetermined frame rate may include photographing the microfluidic apparatus at the predetermined frame rate such that a width of an overlap portion of the successive images is greater than a width of the home mark.

The method may further include increasing a size of an image acquired by the camera as a rotation speed of the microfluidic apparatus increases.

The determining the position of the home of the microfluidic apparatus may include performing an image processing operation with respect to the acquired capture image such that the home mark is located at the center of the image-processed capture image, and determining a position of the home of the microfluidic apparatus by acquiring information which relates to the encoder and which corresponds to the home mark of the image-processed capture image.

In accordance with another aspect of one or more exemplary embodiments, a method for controlling a test apparatus includes arranging a valve of a microfluidic apparatus to be within a predetermined proximity with respect to an energy source, acquiring a first image of the valve by using a camera, arranging a center of the valve to face the energy source by using the acquired first image, and causing the energy source to apply energy to the valve when the center of the valve faces the energy source.

The method may further include acquiring a second image of the valve by using the camera after energy has been applied to the valve, and determining whether to cause additional energy to be applied to the valve by determining an opening state and a closing state of the valve by using the acquired second image of the valve.

The determining whether to cause additional energy to be applied to the valve may include determining whether a remaining amount of a material constituting the valve is greater than a predetermined level by using the acquired second image of the valve, and driving the energy source to apply the additional energy to the valve when the remaining amount of the material constituting the valve is determined to be greater than the predetermined level.

The arranging the center of the valve to face the energy source to face each other may include determining a position difference between the center of the valve and the energy source based on the acquired first image, and controlling a rotation of the microfluidic apparatus and a movement of the energy source such that the center of the valve faces the energy source based on the determined position difference.

The energy source may include a laser source.

In accordance with another aspect of one or more exemplary embodiments, a test apparatus includes a motor configured to cause a microfluidic apparatus to rotate, the motor being in communication with an encoder, a camera configured to photograph the microfluidic apparatus at a predetermined frame rate; and a controller configured to acquire a capture image which includes a home mark of the microfluidic apparatus from among a plurality of images acquired by the camera, to acquire information which relates to the encoder and which corresponds to the home mark of the capture image, and to determine a position of a home of the microfluidic apparatus based on the acquired information.

The camera may be further configured to photograph the home mark of the microfluidic apparatus at a predetermined frame rate such that successive images partially overlap each other.

The camera may be further configured to photograph the microfluidic apparatus at a predetermined frame rate such that a width of an overlap portion of the successive images is greater than a width of the home mark.

The camera may be further configured increase a size of an image as a rotation speed of the microfluidic apparatus increases.

The controller may be further configured to determine the position of the home of the microfluidic apparatus by performing an image processing operation with respect to the acquired capture image such that the home mark is located at the center of the image-processed capture image and by acquiring a pulse of an encoder which corresponds to the home mark of the image-processed capture image.

In accordance with a further aspect of one or more exemplary embodiments, a test apparatus includes a motor configured to cause a microfluidic apparatus to rotate, an energy source configured to apply energy to a valve of the microfluidic apparatus, a camera configured to photograph the microfluidic apparatus, and a controller configured to arrange the center of the valve to face the energy source by using a first image of the valve acquired by the camera and to drive the energy source to apply energy to the valve when the center of the valve faces the energy source.

The camera may be further configured to acquire a second image of the valve after the energy source applies energy to the valve, and the controller may determine whether to apply additional energy to the valve by determining an opening state and a closing state of the valve by using the acquired second image of the valve.

The controller may be further configured to determine whether a remaining amount of a material constituting the valve is greater than a predetermined level by using the acquired second image of the valve, and to drive the energy source to apply the additional energy to the valve when the remaining amount of the material constituting the valve is determined to be greater than the predetermined level.

The controller may be further configured to determine a position difference between the center of the valve and the energy source based on the acquired first image of the valve, and to control a driving of the motor such that the center of the valve faces the energy source based on the determined position difference.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Reference will now be made in detail to exemplary embodiments, examples of which are illustrated in the accompanying drawings, wherein like reference numerals refer to like elements throughout.

Figure 1:
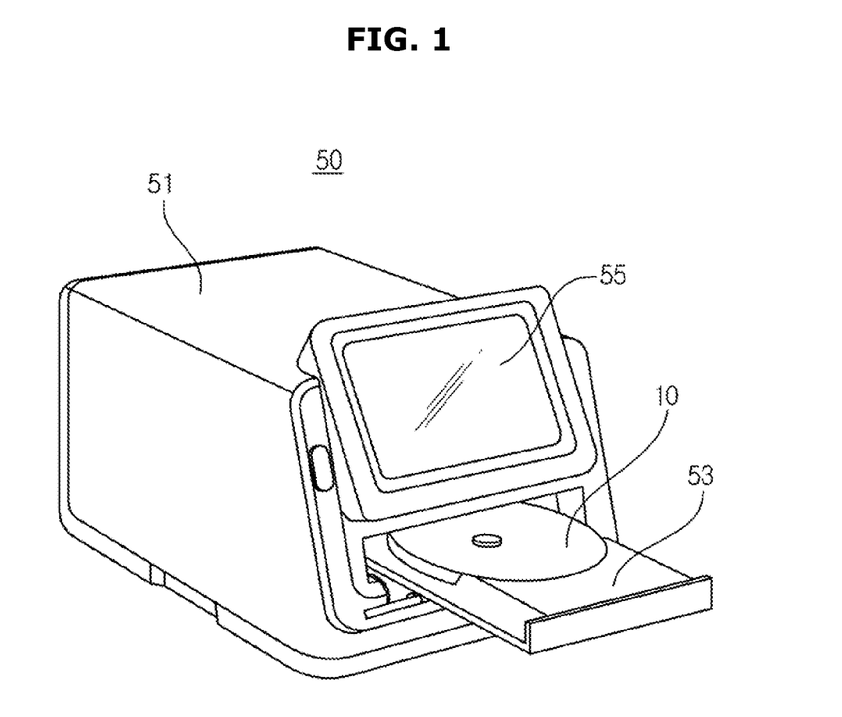
FIG. 1 is a diagram illustrating an appearance of a test apparatus.
Figure 2:
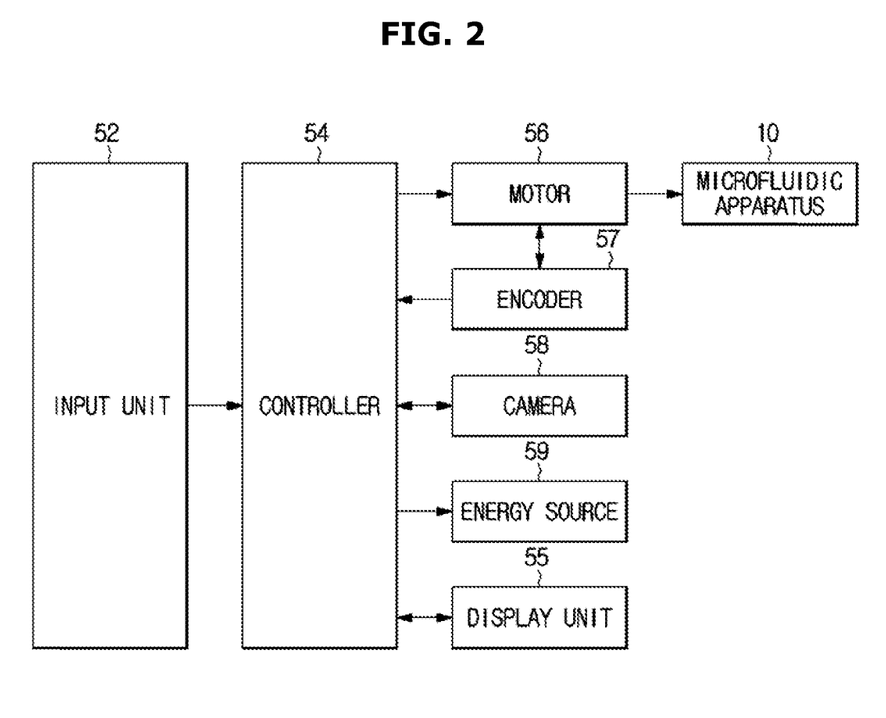
FIG. 2 is a block diagram illustrating a test apparatus.
Figure 3:
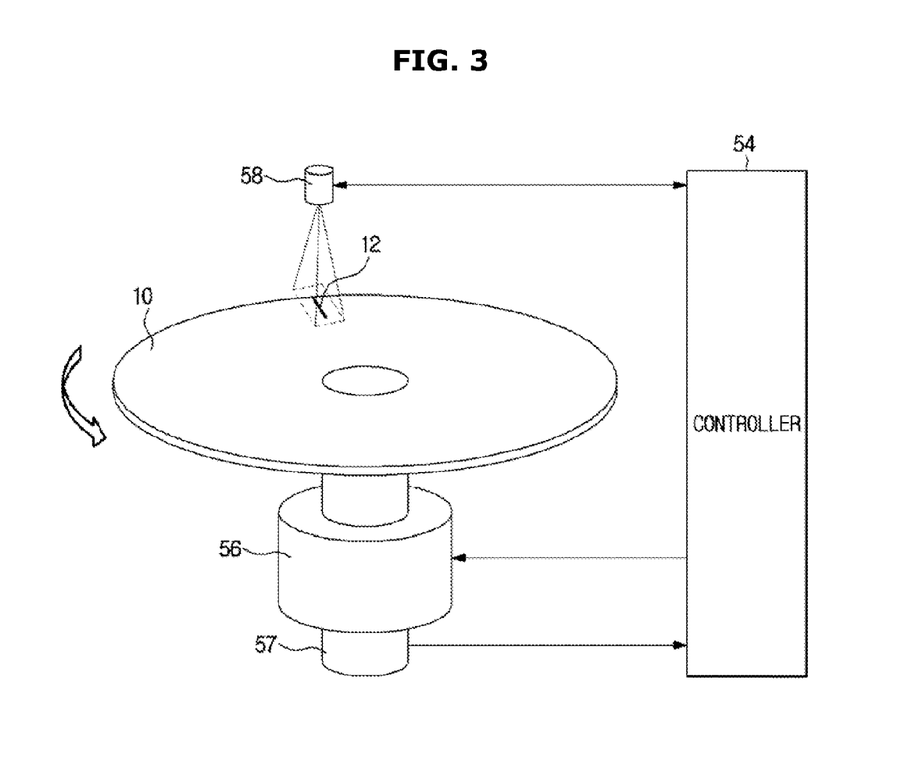
FIG. 3 is a conceptual diagram illustrating photographing of a home mark of a microfluidic apparatus by a camera of a test apparatus.

FIG. 1 is a diagram illustrating an appearance of a test apparatus. FIG. 2 is a block diagram illustrating the test apparatus. FIG. 3 is a conceptual diagram illustrating photographing of a home mark of a microfluidic apparatus by a camera of the test apparatus.

Referring to FIG. 1, when a disk-shaped microfluidic apparatus 10, into which a sample is injected, is loaded on a tray 53 installed in a test apparatus 50, and the tray 53 is inserted into a main body 51 of the test apparatus 50, the test apparatus 50 performs a test by rotating the microfluidic apparatus 10.

The microfluidic apparatus 10 includes a plurality of chambers configured to contain fluids, channels connecting the plurality of chambers, and valves configured to control migration of a sample or a reagent via the channels.

The microfluidic apparatus 10 may be formed by using any one or more of various materials which are easily molded and having a biologically inactive surface, for example, plastic materials, such as acryl (polymethylmethacrylate (PMMA)), polydimethylsiloxane (PDMS), polycarbonate (PC), polypropylene, polyvinyl alcohol, and polyethylene, glass, mica, silica, and silicon wafer. These materials are examples of materials used to form the microfluidic apparatus 10, and exemplary embodiments are not limited thereto. Any material having chemical and biological stabilities, optical transparency, and mechanical processibilty may also be used to form the microfluidic apparatus 10.

The microfluidic apparatus 10 may include a plurality of plates. Space for containing a fluid and passages through which the fluid flows may be provided in the platform 100 by forming groove structures, which correspond to microstructures such as chambers and channels, on the surfaces of two of the plates so as to contact with each other and so as to join the plates together. The joining of the plates may be performed by using any one or more of various methods, such as adhesion by using an adhesive or double-sided adhesive tape, ultrasonic fusion, and laser welding.

Although the disk-shaped microfluidic apparatus 10 is illustrated in FIG. 1, the microfluidic apparatus 10 may also have a self-rotatable disk shape, a fan shape rotatable in a state of being mounted on a rotatable frame, and/or a rotatable polygonal shape.

Since a fluid flow is caused by a centrifugal force in the microfluidic apparatus 10 according to the illustrated exemplary embodiment, chambers receiving the fluid are disposed at outer portions from the center of the microfluidic apparatus 10 with respect to chambers supplying the fluid, which are disposed nearer to the center of the microfluidic apparatus 10.

In order to detect reactions occurring in the microfluidic apparatus 10, positions of the valves, functional units, and chambers disposed on the microfluidic apparatus 10 must be accurately recognized. A point located on the microfluidic apparatus 10 and used as a reference to detect the positions of these valves, functional units, and chambers is referred to as a home, and a mark indicating the home is referred to as a home mark. A home mark 12 is disposed on the front surface of the microfluidic apparatus 10 according to the illustrated exemplary embodiment. As illustrated in FIG. 3, the home mark 12 may be disposed on an outer portion of the front surface of the microfluidic apparatus 10. The home mark 12 may be formed on the front surface of the microfluidic apparatus 10 in a printed form having a predetermined size and a predetermined shape. The test apparatus 50 determines the position of the home of the microfluidic apparatus 10 via recognition of the home mark 12 of the microfluidic apparatus 10. This will be described below in further detail.

A valve, which is disposed in a channel and controls flow of a fluid, may close the channel in order to prevent the fluid from flowing before the valve receives energy from an external device and is thereby opened. Particularly, the valve may be fabricated by mixing a phase transition material and a heat generating fluid. The phase transition material may include any one or more of a wax, a gel, and/or a thermoplastic resin. Examples of the wax may include paraffin wax, examples of the gel may include polyacrylamides, polyacrylates, polymethacrylates, and polyvinylamides, and examples of the thermoplastic resin may include cyclic olefin copolymer (COC), polymethylmethacrylate (PMMA), polycarbonate (PC), polystyrene (PS), polyoxymethylene (POM), perfluoroalkoxy (PFA), polyvinylchloride (PVC), polypropylene (PP), polyethylene terephthalate (PET), polyetheretherketone (PEEK), polyamide (PA), polysulfone (PSU), and polyvinylidene fluoride (PVDF). The heat generating fluid includes a hydrophobic carrier oil and a plurality of heat generating microparticles which are dispersed in the carrier oil. The heat generating microparticles may have a diameter of about several tens of nanometers to several hundreds of nanometers (nm). When energy is supplied to the heat generating microparticles via, for example, a laser beam irradiation, temperature thereof rapidly increases, so that the heat generating microparticles generate heat. The heat generating microparticles may include ferromagnetic metal oxide microparticles. When energy is supplied to the valve from an external device via a laser beam irradiation, or the like, a temperature of the heat generating microparticles rapidly increases. Accordingly, a solid stage valve that closes the channel is melted to have fluidity, thereby opening the channel.

If a sample or a reagent flows along channels respectively from the chambers including the sample and reagent while the microfluidic apparatus 10 is rotated and reactions occur in a particular chamber, the test apparatus 50 detects reaction results of the microfluidic apparatus 10 and displays detection results with respect to test items in order to notify a user of test results after the test is completed.

Referring to FIG. 2, the test apparatus 50 includes an input unit (also referred to herein as an "input device") 52 through which an instruction or a manipulation of a user is received, a motor 56 configured to rotate the microfluidic apparatus 10, a camera 58 configured to photograph the microfluidic apparatus 10, a laser source as an energy source 59 configured to apply energy to valves of the microfluidic apparatus 10 to open the valves, and a display unit (also referred to herein as a "display device" and/or as a "display") 55 configured to display test results of the microfluidic apparatus 10.

The motor 56 is in communication with an encoder 57 and is driven under a control of a controller 54 when the microfluidic apparatus 10 is loaded, thereby causing rotation of the microfluidic apparatus 10. The motor 56 receives a signal which is output from the controller 54, and then repeats rotating and stopping operations, thereby moving a structure disposed on the microfluidic apparatus 10 to a desired position. The encoder 57 may output information which is related to rotations of the motor 56, such as rotation speed and/or rotation angle, to the controller 54, and the controller 54 may control rotation driving of the motor 56 based on the information which is related to the rotation of the motor 56 which is output from the encoder 57.

The camera 58 may be disposed above the microfluidic apparatus 10 so as to photograph the front surface of the microfluidic apparatus 10. Although not shown in the drawings, the camera 58 may be installed in a driving device which is configured to provide a driving force to move the camera 58 in a radial direction. When a driving force is provided to the camera 58 from the driving device under a control of the controller 54, the camera 58 may move in the radial direction and photograph each portion of the microfluidic apparatus 10. The camera 58 may include a complementary metal oxide semiconductor (CMOS) image sensor and/or a charge coupled device (CCD) image sensor and may acquire an image at a frame rate of 60 frames per second. The camera 58 is not limited thereto, and any one or more of known various cameras may also be used.

The energy source 59 is disposed at a portion outside the microfluidic apparatus 10 and supplies energy to a valve of the microfluidic apparatus 10. The energy source 59 that is a light source emitting visible light or infrared light may include a light emitting diode and/or a xenon lamp. The energy source 59 may include a laser source that emits laser beams. The laser source may include a laser diode (LD) and may be configured to emit laser beams to a solidified valve. When the laser source emits a laser beam to the solidified valve, the valve is melted so as to have fluidity by energy supplied by the laser beam, so that opening and closing of the valve may be controlled.

The energy source 59 may be disposed above the microfluidic apparatus 10 or at a driving device (not shown) which provides a driving force to move the energy source 59 in a radial direction of the microfluidic apparatus 10. The driving device may include a motor that provides a driving force for moving the energy source 59.

When a valve of a channel to be open moves along a radial line where the energy source 59 is located by rotation of the motor 56, the energy source 59 moves in a radial direction to a position facing the valve and applies energy to the valve. Via the movement of the microfluidic apparatus 10 in an azimuthal direction by the rotation of the motor 56 and the movement of the energy source 59 in the radial direction, energy may accurately be applied to the valve of the channel so as to be open. One driving device which is capable of moving both of the energy source 59 and the camera 58 in the radial direction may be used. Alternatively, two separate driving devices respectively moving the energy source 59 and the camera 58 may be used.

The test apparatus 50 according to the illustrated exemplary embodiment uses images of the microfluidic apparatus 10 which have been acquired by the camera 58 in order to determine the position of the home of the microfluidic apparatus 10. Hereinafter, a method for determining the home of the microfluidic apparatus 10 will be described in further detail.

The controller 54 drives the motor 56 in order to rotate the microfluidic apparatus 10 and drives the camera 58 while the microfluidic apparatus 10 is rotated to enable the camera 58 to photograph the microfluidic apparatus 10.

The controller 54 controls a rotation speed of the motor 56 such that the microfluidic apparatus 10 is rotated at a substantially constant speed. While the motor 56 rotates, the encoder 57 of the motor 56 acquires information which is related to rotation of the motor 56 and outputs the acquired information to the controller 54.

As illustrated in FIG. 3, the camera 58 may be disposed at a position so as to be facing the home mark 12, or may move to the position while the microfluidic apparatus 10 is rotated so as to photograph the home mark 12, which is disposed at an outer portion of the front surface of the microfluidic apparatus 10. As described above, when the camera 58 is installed at the driving device which is capable of moving the camera 58 in a radial direction, the driving device moves the camera 58 in the radial direction to locate the camera 58 on the same radial line as the home mark 12 in accordance with a control of the controller 54.

The controller 54 may control shooting conditions of the camera 58 in accordance with the rotation speed of the motor 56 in order to prevent the camera 58 from missing the home mark 12 and/or to prevent the camera 58 from photographing only a portion of the home mark 12 while the microfluidic apparatus 10 is rotated.

Figure 4:
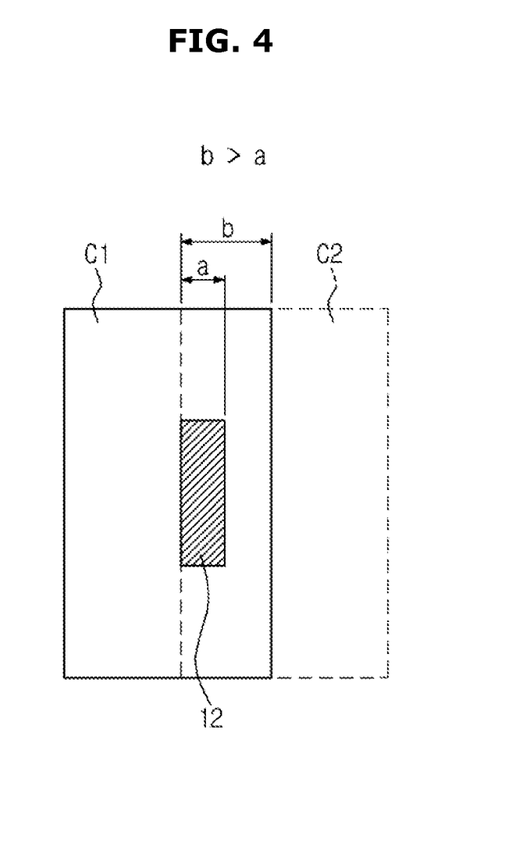
FIG. 4 is a conceptual diagram illustrating images acquired by a camera of a test apparatus and partially overlapping each other.
Figure 5:
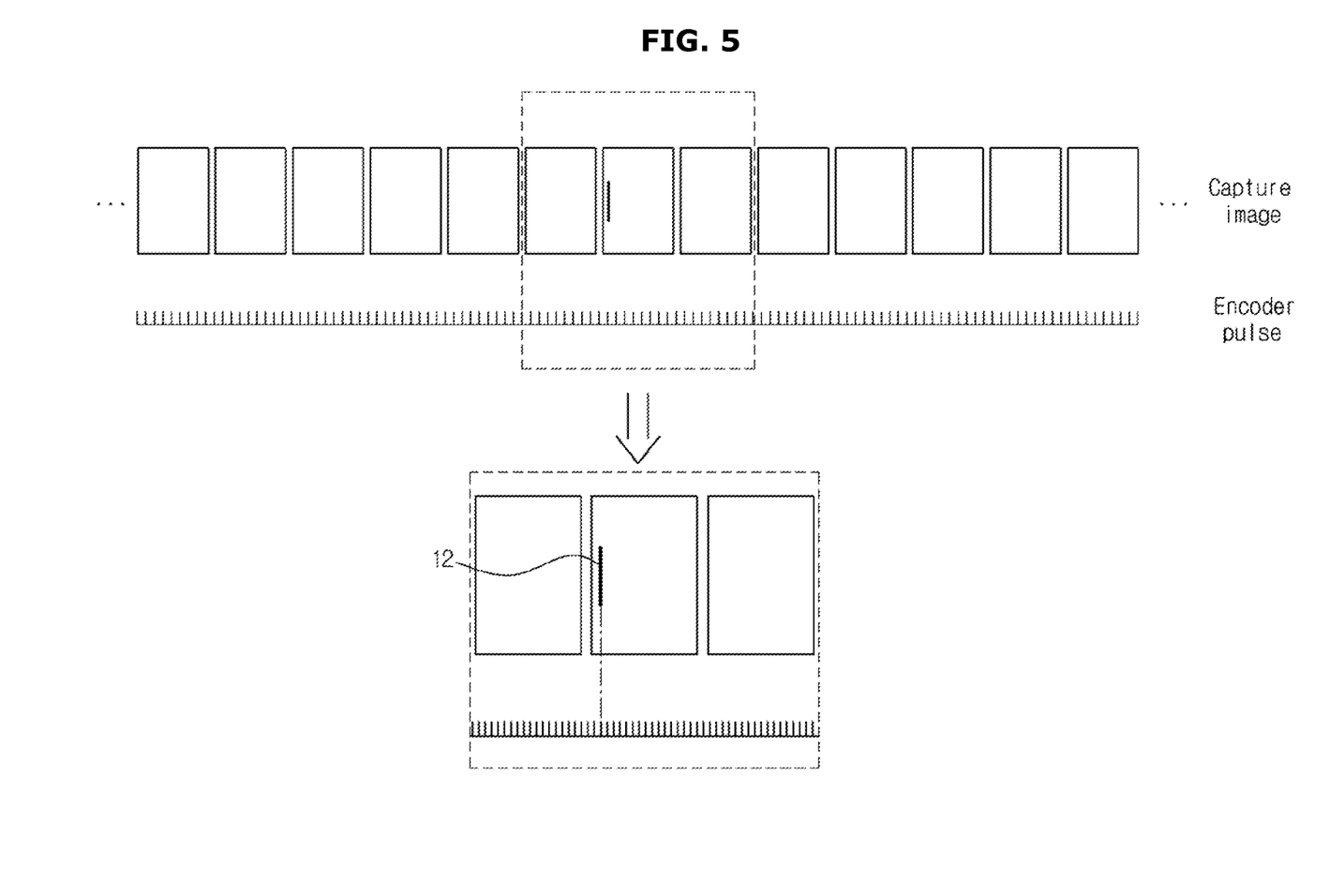
FIG. 5 is a conceptual diagram illustrating a capture image including a home mark of a microfluidic apparatus from among a plurality of images acquired by a camera of a test apparatus and pulse information of an encoder which corresponds to the capture image.

FIG. 4 is a conceptual diagram illustrating images acquired by the camera 58 of the test apparatus and partially overlapping each other. FIG. 5 is a conceptual diagram illustrating a capture image of the home mark 12 of the microfluidic apparatus 10 from among a plurality of images acquired by the camera 58 of the test apparatus and pulse information of the encoder 57 which corresponds to the capture image.

The camera 58 photographs the microfluidic apparatus 10 such that portions of consecutive capture images C1 and C2 overlap each other, as illustrated in FIG. 4. The camera 58 photographs the microfluidic apparatus 10 such that a width b of an overlap portion is greater than a width a of the home mark 12, as illustrated in FIG. 4. When the camera 58 captures images without having an overlap portion, the home mark 12 may not be photographed by the camera 58. When the width b of the overlap portion is less than the width a of the home mark 12, only a portion of the home mark 12 may be captured, although there is an image which includes the home mark 12. Thus, the controller 54 controls shooting conditions of the camera 58 such that consecutively acquired images by the camera 58 overlap each other and the width b of the overlap portion is greater than the width a of the home mark 12.

If a home mark 12 of a microfluidic apparatus 10 having a diameter of 120 mm and a circumference of 377 mm is photographed by the camera 58 at a frame rate of 60 fps while the microfluidic apparatus 10 is rotated at a speed of 30 rpm, and a frame size of the image acquired by the camera 58 is controlled to have a width of 3.14 mm or greater, the microfluidic apparatus 10 may capture an image which includes the home mark 12 without missing the same. More precisely, if the width of the home mark 12 is 100 um, and the frame size of the image is controlled to have a width of 3.3 mm or greater, the width of the overlap portion of the two consecutive images is greater than the width of the home mark 12, and thus the camera 58 may capture the home mark 12 without missing the home mark 12.

Alternatively, if the home mark 12 of the same microfluidic apparatus 10 is photographed by the camera 58 at a frame rate of 60 fps while the microfluidic apparatus 10 is rotated at a speed of 60 rpm, and a frame size of the image acquired by the camera 58 is controlled to have a width of 6.28 mm or greater, the microfluidic apparatus 10 may capture an image which includes the home mark 12 without missing the home mark 12. More precisely, if the width of the home mark 12 is 100 um, and the frame size of the image may be controlled to have a width of 6.4 mm or greater, the width of the overlap portion of the two consecutive images is greater than the width of the home mark 12, and thus the camera 58 may capture the home mark 12 without missing the home mark 12.

As described above, when the camera 58 photographs the microfluidic apparatus 10 while the microfluidic apparatus 10 is rotated, a plurality of images may be acquired as illustrated in FIG. 5. Since the plurality of acquired images includes a capture image of the home mark 12, the controller 54 searches for the capture image which includes the home mark 12 from among the plurality of images. The controller 54 detects the position of the home mark 12 from the capture image via image processing, and determines a pulse of the encoder 57 which corresponds to the detected position of the home mark 12, thereby determining the position as a position of the home of the microfluidic apparatus 10.

When the home mark 12 is not located at the center of the capture image but at a side thereof, it may be difficult to determine a pulse of the encoder 57 precisely which pulse corresponds to the home mark 12. For the more precise determination of the position of the home, the controller 54 may perform an image processing operation such that the home mark 12 is located at the center of the capture image and determine the pulse of the encoder 57 corresponding to the home mark 12 based on the image-processed image.

When the position of the home of the microfluidic apparatus 10 is determined, the controller 54 determines positions of respective structures of the microfluidic apparatus 10 with reference to the determined position of the home, and performs a test by using the microfluidic apparatus 10.

The aforementioned method for determining the position of the home of the microfluidic apparatus 10 will be described below with reference to the flowchart of FIG. 6, which illustrates a method for controlling the test apparatus to determine the position of the home of the microfluidic apparatus 10.

Figure 6:
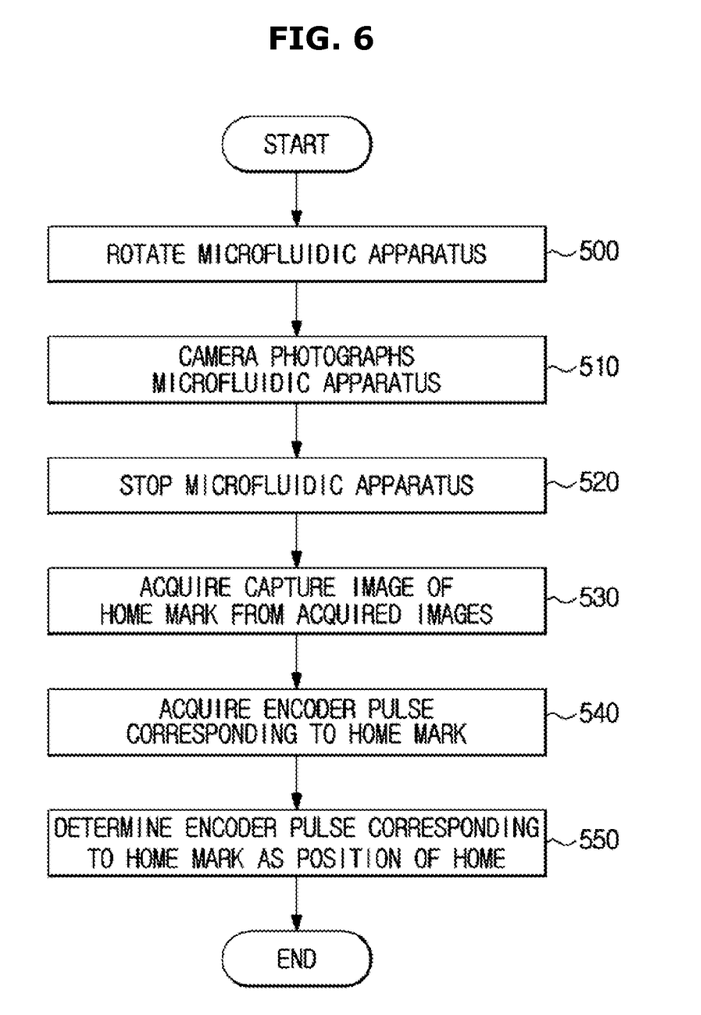
FIG. 6 is a flowchart illustrating a method of controlling a test apparatus to determine a position of a home mark of a microfluidic apparatus.

Referring to FIG. 6, in operation 500, the controller 54 rotates the microfluidic apparatus 10, and in operation 510, the camera 58 photographs the microfluidic apparatus 10 while the microfluidic apparatus 10 is rotated. After photographing of the microfluidic apparatus 10 is completed, in operation 520, the controller 54 stops the rotation of the microfluidic apparatus 10.

The controller 54 drives the motor 56 to rotate the microfluidic apparatus 10 and drives the camera 58 while the microfluidic apparatus 10 is rotated in order to enable the camera 58 to photograph the microfluidic apparatus 10. The controller 54 controls a rotation speed of the motor 56 such that the microfluidic apparatus 10 is rotated at a constant speed. While the motor 56 rotates, the encoder 57 acquires information which relates to the rotation of the motor 56 and outputs the information to the controller 54. As illustrated in FIG. 3, the camera 58 may be disposed at a position facing the home mark 12, or may move to the position so as to photograph the home mark 12 which is disposed at an outer portion of the front surface of the microfluidic apparatus 10 while the microfluidic apparatus 10 is rotated. As described above, when the camera 58 is installed at the driving device which is capable of moving the camera 58 in a radial direction, the driving device moves the camera 58 in the radial direction in order to locate the camera 58 along the same radial line as the home mark 12 in accordance with a control of the controller 54. The controller 54 may control shooting conditions of the camera 58 in accordance with the rotation speed of the motor 56 in order to prevent the camera 58 from missing the home mark 12 and/or from photographing only a portion of the home mark 12 while the microfluidic apparatus 10 is rotated. The camera 58 may photograph the microfluidic apparatus 10 such that portions of consecutive capture images overlap each other, as illustrated in FIG. 4. The camera 58 photographs the microfluidic apparatus 10 such that a width b of an overlap portion is greater than a width a of the home mark 12, as illustrated in FIG. 4. When the camera 58 captures images without having an overlap portion, the home mark 12 may not be photographed by the camera 58. When the width b of the overlap portion is less than the width a of the home mark 12, only a portion of the home mark 12 may be captured although there is an image which includes the home mark 12. Thus, the controller 54 controls shooting conditions of the camera 58 such that consecutively acquired images by the camera 58 overlap each other and the width b of the overlap portion is greater than the width a of the home mark 12.

If a home mark 12 of a microfluidic apparatus 10 having a diameter of 120 mm and a circumference of 377 mm is photographed by the camera 58 at a frame rate of 60 fps while the microfluidic apparatus 10 is rotated at a speed of 30 rpm, and a frame size of the image acquired by the camera 58 is controlled to have a width of 3.14 mm or greater, the microfluidic apparatus 10 may capture an image which includes the home mark 12 without missing the same. More precisely, if the width of the home mark 12 is 100 um, and the frame size of the image is controlled to have a width of 3.3 mm or greater, the width of the overlap portion of the two consecutive images is greater than the width of the home mark 12, and thus the camera 58 may capture the home mark 12 without missing the home mark 12.

Alternatively, if the home mark 12 of the same microfluidic apparatus 10 is photographed by the camera 58 at a frame rate of 60 fps while the microfluidic apparatus 10 is rotated at a speed of 60 rpm, and a frame size of the image acquired by the camera 58 is controlled to have a width of 6.28 mm or greater, the microfluidic apparatus 10 may capture an image which includes the home mark 12 without missing the home mark 12. More precisely, if the width of the home mark 12 is 100 um, and the frame size of the image may be controlled to have a width of 6.4 mm or greater, the width of the overlap portion of the two consecutive images is greater than the width of the home mark 12, and thus the camera 58 may capture the home mark 12 without missing the home mark 12.

When the camera 58 photographs the microfluidic apparatus 10, in operation 530, the controller 54 acquires a capture image which includes the home mark 12 and, in operation 540, the controller 54 acquires a pulse of the encoder 57 which pulse corresponds to the home mark 12. Then, in operation 550, the controller 54 determines the acquired pulse of the encoder 57 as corresponding to the position of the home.

When the camera 58 photographs the microfluidic apparatus 10 while the microfluidic apparatus 10 is rotated, a plurality of images may be acquired, as illustrated in FIG. 5. Since the plurality of acquired images includes a capture image of the home mark 12, the controller 54 searches for the capture image which includes the home mark 12 from among the plurality of images. The controller 54 detects the position of the home mark 12 from the capture image via image processing, and determines a pulse of the encoder 57 which pulse corresponds to the detected position of the home mark 12, thereby determining the position as a position of the home of the microfluidic apparatus 10. When the home mark 12 is not located at the center of the capture image but at a side thereof, it may be difficult to determine a pulse of the encoder 57 which precisely corresponds to the home mark 12. For the more precise determination of the position of the home, the controller 54 may perform an image processing operation such that the home mark 12 is located at the center of the capture image, and determine the pulse of the encoder 57 which corresponds to the home mark 12 based on the image-processed image. When the position of the home of the microfluidic apparatus 10 is determined, the controller 54 determines positions of respective structures of the microfluidic apparatus 10 with reference to the determined position of the home, and performs a test by using the microfluidic apparatus 10.

Figure 7:
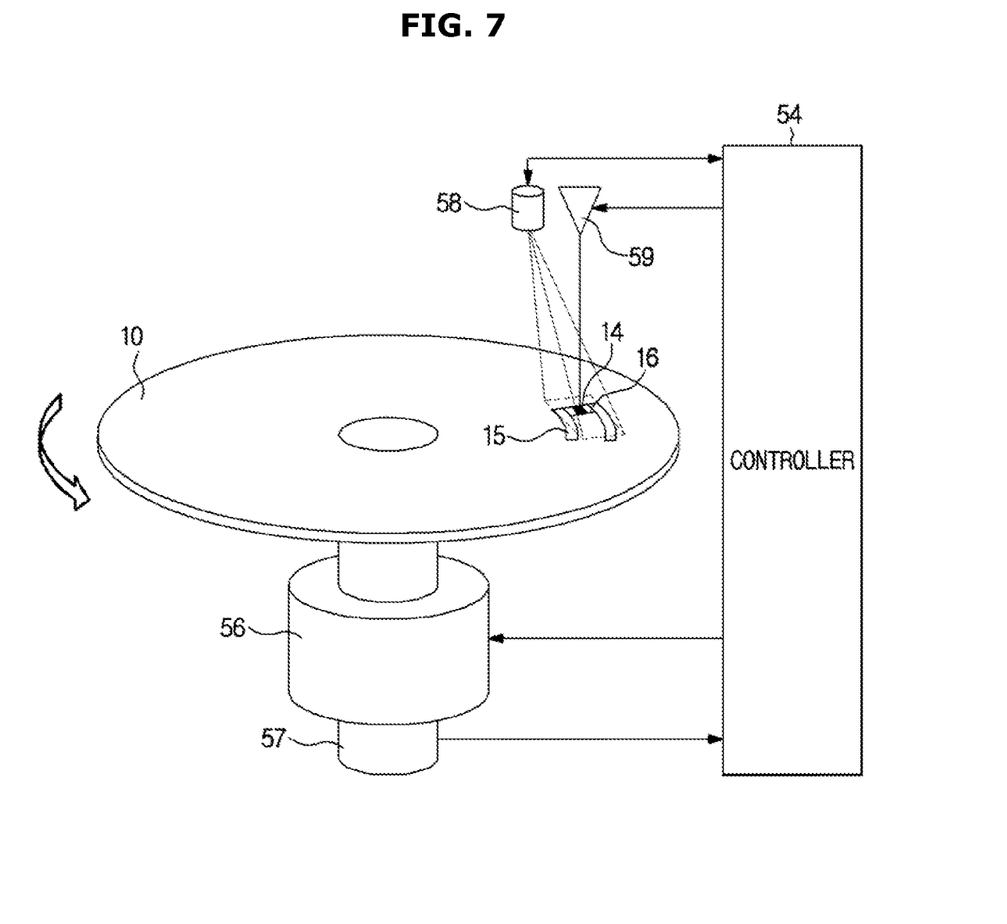
FIG. 7 is a conceptual diagram illustrating photographing of a valve of a microfluidic apparatus by a camera of a test apparatus.
Figure 8:
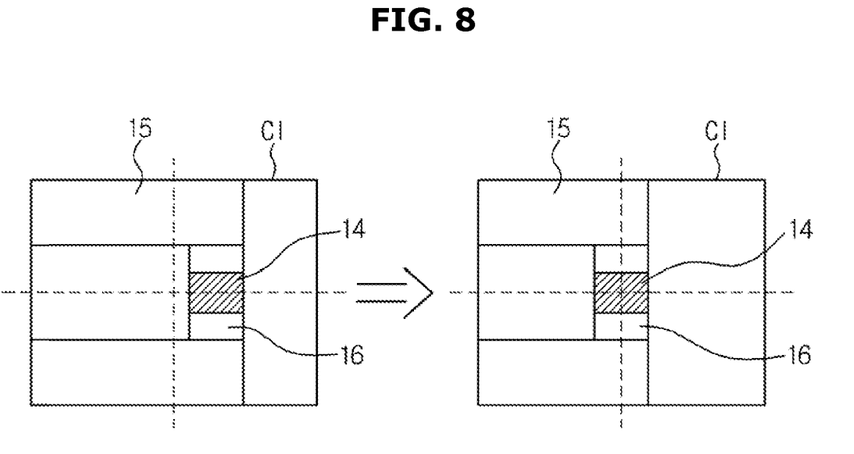
FIG. 8 is a conceptual diagram illustrating arranging the center of a valve to face a laser source by using an image captured by a camera of a test apparatus.
Figure 9:
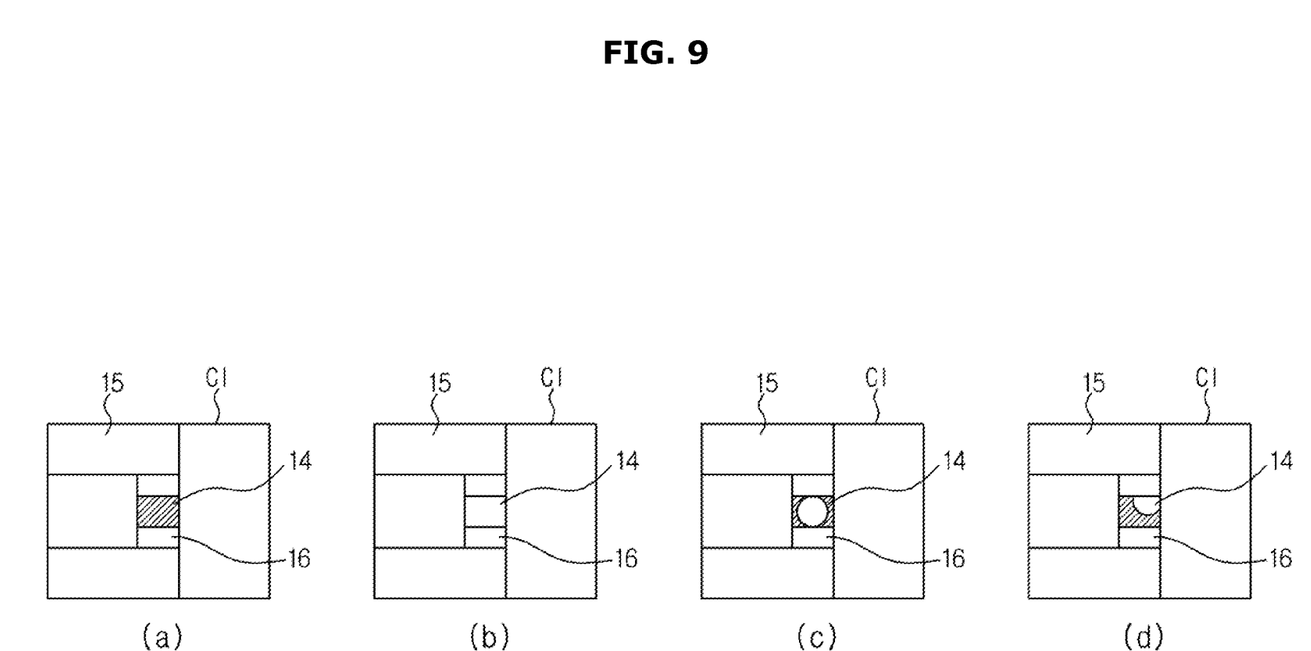
FIG. 9 illustrates valve images captured by a camera of a test apparatus.

The test apparatus 50 according to the illustrated exemplary embodiment may more precisely control the opening and closing of the valve 14 by using the camera 58. This will be described with reference to the following drawings, hereinbelow. FIG. 7 is a conceptual diagram illustrating photographing of a valve 14 of a microfluidic apparatus by a camera 58 of a test apparatus. FIG. 8 is a conceptual diagram illustrating an arrangement of the center of the valve 14 to face a laser source by using an image acquired by the camera 58 of the test apparatus. FIG. 9 illustrates images of the valve 14 captured by the camera 58 of the test apparatus.

Referring to FIG. 7, the controller 54 drives the motor 56 to rotate the microfluidic apparatus 10 such that the valve 14 to be opened moves to a position so as to be facing an energy source 59 which is capable of applying energy to the valve 14 by using, for example, a laser beam, and the controller 54 moves the energy source 59 in a radial direction.

When the valve 14 of the microfluidic apparatus 10 and the energy source 59 are moved to positions which face each other, the controller 54 drives the camera 58 to photograph the valve 14 of the microfluidic apparatus 10.

As illustrated in FIG. 7, the controller 54 may move the camera 58 to a position where the camera 58 may photograph the valve 14 to be opened. As described above, when the camera 58 is installed at the driving device which is capable of moving the camera 58 in a radial direction, the driving device may move the camera 58 in the radial direction in order to locate the camera 58 near a position which faces the valve 14 in accordance with a control of the controller 54.

When the energy source 59 and the camera 58 are located to face the valve 14 to be opened, the controller 54 drives the camera 58 to photograph the valve 14 before driving the energy source 59. When the camera 58 photographs the valve 14 and acquires a capture image which includes the valve 14, the controller 54 may perform an image processing operation, such as a process of adjusting color of the valve 14, such that the valve 14 is clearly distinguished from surrounding structures in the image-processed capture image. Through such a process, a more precise analysis may be conducted by using the images.

When the camera 58 photographs the valve 14 to be opened as illustrated in FIG. 7, and the capture image which includes the valve 14 is acquired as illustrated in FIG. 8, the controller 54 rotates the microfluidic apparatus 10 and moves the energy source 59 by using the image such that the valve 14 and the energy source 59 more precisely face each other. As illustrated in FIG. 8, the controller 54 determines the center of the valve 14 in the capture image of the valve 14 and calculates a position difference between the center of the valve 14 and the energy source 59 by using the capture image of the valve 14. The controller 54 drives the motor 56 that rotates the microfluidic apparatus 10 and the driving device that moves the energy source 59 in a radial direction so as to reduce the calculated position difference, such that the center of the valve 14 and the energy source 59 are located at the same position, as illustrated in a right image of FIG. 8. The position difference between the center of the valve 14 and the energy source 59 may be represented by a distance between the center of the valve 14 and the energy source 59 in the radial direction and an angle difference between the center of the valve 14 and the energy source 59 with respect to a rotation center of the microfluidic apparatus 10. The distance between the center of the valve 14 and the energy source 59 in the radial direction may be reduced and/or eliminated by moving the energy source 59 in the radial direction, and the angle difference between the center of the valve 14 and the energy source 59 with respect to the rotation center of the microfluidic apparatus 10 may be reduced and/or eliminated by rotating the microfluidic apparatus 10.

As such, when the center of the valve 14 and the energy source 59 face each other, the controller 54 drives the energy source 59 such that energy is applied to the valve 14 from the energy source 59. As described above, a laser source that emits laser beams may be used as the energy source 59.

In general, when energy is applied to the valve 14, and the valve 14 is melted, the microfluidic apparatus 10 is rotated so as to transport the sample or reagent in the chamber 15 through the open channel 16. According to the illustrated exemplary embodiment, however, the microfluidic apparatus 10 is not immediately rotated, and it is confirmed whether the channel 16 is sufficiently open to allow for transport the sample and reagent through the channel 16 by using the camera 58.

In particular, when an application of energy from the energy source 59 to the valve 14 is completed, the controller 54 drives the camera 58 to photograph the valve 14 once more. The capture image of the valve 14 acquired by the camera 58 may include an image in which the valve 14 is melted and the channel 16 is open, as illustrated in drawing (b) of FIG. 9, and images in which the valve 14 is not sufficiently melted and the channel 16 is not sufficiently open, as illustrated in drawing (c) and drawing (d) of FIG. 9. A state which exists before energy is applied to the valve 14 such that the valve 14 is closed is illustrated in drawing (a) of FIG. 9.

When the image of the valve 14 acquired by the camera 58 is an image in which the valve 14 is sufficiently melted and the channel 16 is sufficiently open, as illustrated in drawing (b) of FIG. 9, the controller 54 performs a predetermined test operation, such as rotating of the microfluidic apparatus 10 to transport the sample or reagent.

However, when the image of the valve 14 acquired by the camera 58 is an image in which the valve 14 is not sufficiently melted and the channel 16 is partially closed, as illustrated in drawing (c) and drawing (d) of FIG. 9, the controller 54 drives the energy source 59 once more so as to cause a melting of the remainder of the valve 14. For example, the controller 54 may determine whether an amount of the remainder of the valve 14 is greater than a predetermined level by using the image of the valve 14. When the amount of the remainder is greater than the predetermined level, the controller 54 may drive the energy source 59 to apply additional energy so as to cause further melting of the valve 14.

If the microfluidic apparatus 10 is rotated to transport the sample or reagent while the valve 14 is not completely melted and the channel 16 is not sufficiently open, the sample or reagent cannot efficiently move through the channel 16. As a result, the test cannot be properly performed. Thus, according to the illustrated exemplary embodiment, the open state of the channel 16 may be determined by checking the melting state of the valve 14 by using the image of the valve 14 which has been subsequently photographed by the camera 58. According to the result, the process of driving the energy source 59 may be performed once more in order to completely open the channel 16. The controller 54 may repeatedly perform this procedure until the channel 16 is completely open.

The aforementioned method for opening the valve 14 will be described with reference to FIG. 10 which illustrates a method for controlling a test apparatus for opening the valve 14 of the microfluidic apparatus 10.

Figure 10:
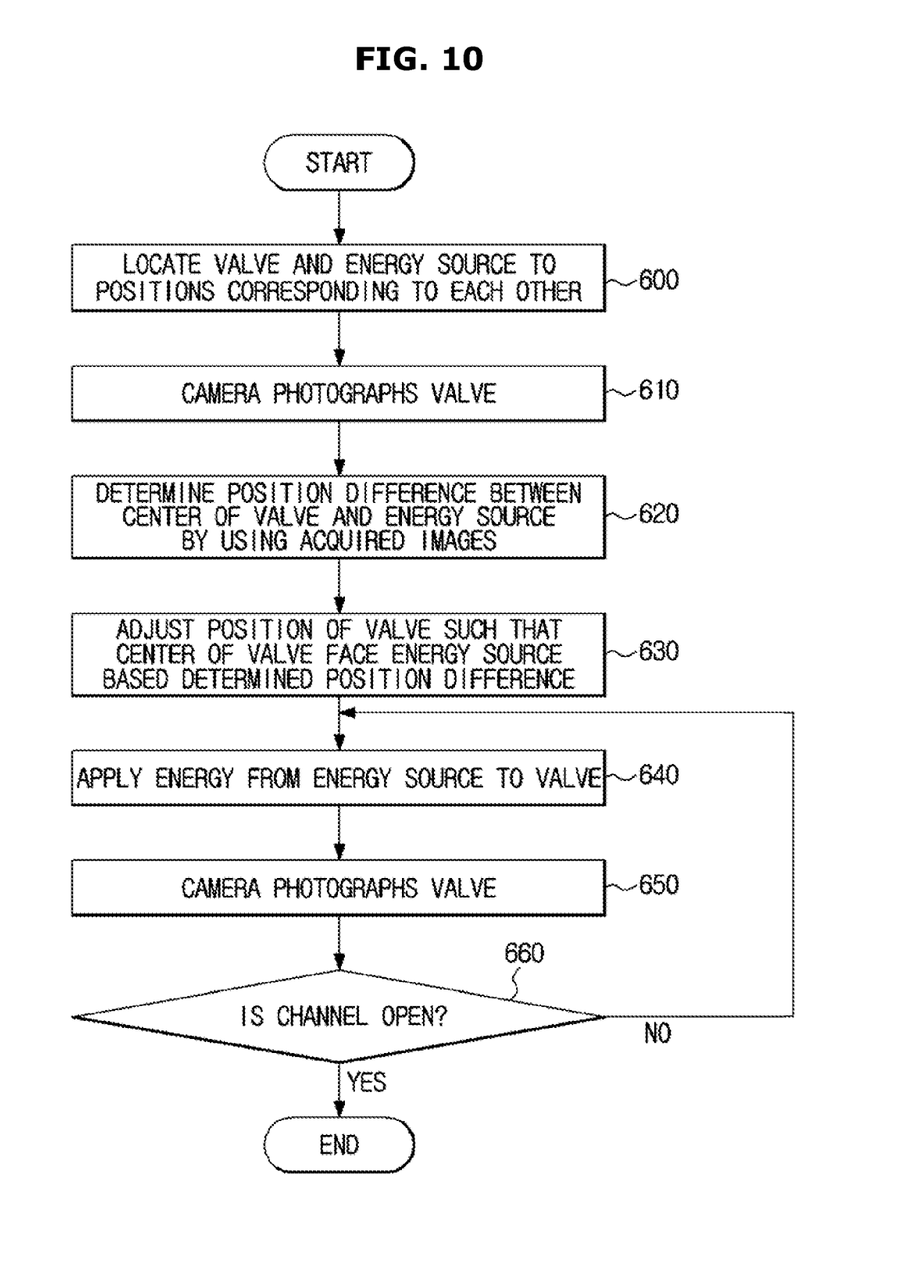
FIG. 10 is a flowchart illustrating a method for controlling a test apparatus for opening of a valve of a microfluidic apparatus.

Referring to FIG. 10, in operation 600, the controller 54 locates the valve 14 and the energy source 59 to correspond to each other, and in operation 610, the controller 54 drives the camera 58 to photograph the valve 14.

As illustrated in FIG. 7, the controller 54 drives the motor 56 to rotate the microfluidic apparatus 10 such that the valve 14 to be opened moves to a position which faces the energy source 59 which is capable of applying energy to the valve 14 by using, for example, a laser beam, and the controller 54 moves the energy source 59 in a radial direction. When the valve 14 of the microfluidic apparatus 10 and the energy source 59 move to positions which are facing each other, the controller 54 drives the camera 58 to photograph the valve 14 of the microfluidic apparatus 10. As illustrated in FIG. 7, the controller 54 may move the camera 58 to a position where the valve 14 to be opened may be photographed by the camera 58. As described above, when the camera 58 is installed at the driving device which is capable of moving the camera 58 in a radial direction, the driving device moves the camera 58 in the radial direction so as to arrange the camera 58 near a position which faces the valve 14 in accordance with a control of the controller 54. When the energy source 59 and the camera 58 are arranged so as to face the valve 14 to be opened, the controller 54 drives the camera 58 to photograph the valve 14 before driving the energy source 59. When the camera 58 photographs the valve 14 and acquires a capture image which includes the valve 14, the controller 54 may perform an image processing operation, such as a process of adjusting color of the valve 14, such that the valve 14 is clearly distinguished from surrounding structures in the capture image. Through such a process, a more precise analysis may be conducted by using the images.

When the camera 58 photographs the valve 14, in operation 620, the controller 54 determines a position difference between the center of the valve 14 and the energy source 59 by using the capture images, and in operation 630, the controller 54 adjusts the position of the valve 14 such that the center of the valve 14 faces the energy source 59 based on the determined position difference. When the center of the valve 14 and the energy source 59 face each other, in operation 640, the controller 54 drives the energy source 59 such that energy is applied to the valve 14 from the energy source 59.

When the camera 58 photographs the valve 14 to be opened as illustrated in FIG. 7, and the capture image which includes the valve 14 is acquired as illustrated in FIG. 8, the controller 54 rotates the microfluidic apparatus 10 and moves the energy source 59 by using the image such that the valve 14 and the energy source 59 more precisely face each other. As illustrated in FIG. 8, the controller 54 determines the center of the valve 14 in the capture image of the valve 14 and calculates a position difference between the center of the valve 14 and the energy source 59 by using the capture image of the valve 14. The controller 54 drives the motor 56 that rotates the microfluidic apparatus 10 and the driving device that moves the energy source 59 in a radial direction so as to reduce and/or eliminate the calculated position difference, such that the center of the valve 14 and the energy source 59 are located at the same position, as illustrated in the right image of FIG. 8. The position difference between the center of the valve 14 and the energy source 59 may be represented by a distance between the center of the valve 14 and the energy source 59 in the radial direction and an angle difference between the center of the valve 14 and the energy source 59 with respect to a rotation center of the microfluidic apparatus 10. The distance between the center of the valve 14 and the energy source 59 in the radial direction may be reduced and/or substantially eliminated by moving the energy source 59 in the radial direction, and the angle difference between the center of the valve 14 and the energy source 59 with respect to the rotation center of the microfluidic apparatus 10 may be reduced and/or substantially eliminated by rotating the microfluidic apparatus 10. As such, when the center of the valve 14 and the energy source 59 face each other, the controller 54 drives the energy source 59 such that energy is applied to the valve 14 from the energy source 59. As described above, a laser source that emits laser beams may be used as the energy source 59. In general, when energy is applied to the valve 14, and the valve 14 is melted, the microfluidic apparatus 10 is rotated to move the sample or reagent through the open channel 16. According to the illustrated exemplary embodiment, however, the microfluidic apparatus 10 is not immediately rotated, and it is confirmed whether the channel 16 is sufficiently open to move the sample and reagent through the channel 16 by using the camera 58.

When energy is applied from the energy source 59 to the valve 14, in operation 650, the controller 54 drives the camera 58 to photograph the valve 14 again. Then, in operation 660, the controller 54 determines whether the channel 16 is open by using images acquired by photographing the valve 14 after the energy has been applied to the valve.

When application of energy from the energy source 59 to the valve 14 is completed, the controller 54 drives the camera 58 to photograph the valve 14 once more. The images of the valve 14 acquired by the camera 58 may include an image in which the valve 14 is melted and the channel 16 is open, as illustrated in drawing (b) of FIG. 9, and images in which the valve 14 is not sufficiently melted and the channel 16 is not sufficiently open, as illustrated in drawing (c) and drawing (d) of FIG. 9. A state which exists before energy has been applied to the valve 14 is illustrated in drawing (a) of FIG. 9. When the image of the valve 14 acquired by the camera 58 is an image in which the valve 14 is completely melted and the channel 16 is sufficiently open, as illustrated in drawing (b) of FIG. 9, the controller 54 performs a predetermined test operation, such as rotating of the microfluidic apparatus 10 to move the sample or reagent. However, when the image of the valve 14 acquired by the camera 58 is an image in which the valve 14 is not completely melted and the channel 16 is partially closed, as illustrated in drawing (c) and drawing (d) of FIG. 9, the controller 54 drives the energy source 59 once more to melt the remainder of the valve 14. For example, the controller 54 may determine whether an amount of the remainder of the valve 14 is greater than a predetermined level by using the image of the valve 14. When the amount of the remainder is greater than the predetermined level, the controller 54 may drive the energy source 59 to apply additional energy in order to cause further melting of the valve 14.

If the microfluidic apparatus 10 is rotated to move the sample or reagent while the valve 14 is not completely melted and the channel 16 is not sufficiently open, the sample or reagent cannot sufficiently move through the channel 16. As a result, the test cannot be properly performed. Thus, according to the illustrated exemplary embodiment, the open state of the channel 16 may be determined by checking the melting state of the valve 14 by using the image of the valve 14 which is acquired by the camera 58 after the further application of energy has been completed. According to the result, the process of operating the energy source 59 to apply additional energy to the valve 14 may be performed to completely open the channel 16. The controller 54 may repeatedly perform this procedure until the channel 16 is completely open.

As is apparent from the above description, the position of the home may be precisely determined by using the capture image of the home mark which is acquired by the camera.

In addition, according to the illustrated exemplary embodiments, feedback information with regard to opening or closing of the valve may be received by using the images of the valve acquired by the camera. When the valve is not completely open, a laser beam may be repeatedly applied to the valve in order to completely open the valve.

Although a few exemplary embodiments have been shown and described, it will be appreciated by those skilled in the art that changes may be made in these exemplary embodiments without departing from the principles and spirit of the present inventive concept, the scope of which is defined in the claims and their equivalents.

What is claimed is:

1. A method for controlling a test apparatus, the method comprising:
   photographing a microfluidic apparatus at a predetermined shooting speed by using a camera of the test apparatus while the microfluidic apparatus is rotating at a predetermined speed;
   acquiring a capture image which comprises a home mark of the microfluidic apparatus, wherein the acquired capture image is included among a plurality of images acquired by the camera; and
   acquiring information which relates to an encoder of the test apparatus and which correspond to the home mark of the capture image, and determining a position of a home of the microfluidic apparatus based on the acquired information, wherein the photographing of the microfluidic apparatus at the predetermined shooting speed comprises photographing the microfluidic apparatus at the predetermined shooting speed such that successive images partially overlap each other to include at least a portion of the home mark.

2. The method according to claim 1, wherein the photographing of the microfluidic apparatus at the predetermined shooting speed comprises photographing the microfluidic apparatus at the predetermined shooting speed such that a width of an overlap portion of the successive images is greater than a width of the home mark.

3. The method according to claim 1, wherein the shooting speed of the camera comprises a frame rate.

4. The method according to claim 1, further comprising increasing a size of an image acquired by the camera as a rotation speed of the microfluidic apparatus increases.

5. The method according to claim 1, wherein the determining the position of the home of the microfluidic apparatus comprises:

performing an image processing operation with respect to the acquired capture image such that the home mark is located at an approximate center of the image-processed capture image; and determining a position of the home of the microfluidic apparatus by acquiring information which relates to the encoder and which corresponds to the home mark of the image-processed capture image.

6. A test apparatus comprising:

a motor configured to cause a microfluidic apparatus to rotate, the motor being in communication with an encoder;

a camera configured to photograph the microfluidic apparatus at a predetermined shooting speed; and a controller configured to acquire a capture image which comprises a home mark of the microfluidic apparatus from among a plurality of images acquired by the camera, to acquire information which relates to the encoder and which corresponds to the home mark of the capture image, and to determine a position of a home of the microfluidic apparatus based on the acquired information, wherein the camera is further configured to photograph the home mark of the microfluidic apparatus at a predetermined shooting speed such that successive images partially overlap each other to include at least a portion of the home mark.

7. The test apparatus according to claim 6, wherein the camera is further configured to photograph the microfluidic apparatus at a predetermined shooting speed such that a width of an overlap portion of the successive images is greater than a width of the home mark.

8. The test apparatus according to claim 6, wherein the camera is configured to photograph the microfluidic apparatus at a predetermined frame rate.

9. The test apparatus according to claim 6, wherein the camera is further configured to increase a size of an image as a rotation speed of the microfluidic apparatus increases.

10. The test apparatus according to claim 6, wherein the controller is further configured to determine the position of the home of the microfluidic apparatus by performing an image processing operation with respect to the acquired capture image such that the home mark is located at an approximate center of the image-processed capture image and by acquiring a pulse of an encoder which corresponds to the home mark of the image-processed capture image.

* * * * *